United States Patent [19]

Michielli et al.

[11] Patent Number: 5,507,832
[45] Date of Patent: Apr. 16, 1996

[54] PROSTHESIS WITH INTEGRAL PROXIMAL SPACER

[75] Inventors: Michael Michielli, Hoboken; Glen Kashuba, River Edge; J. Mel Goldenberg, Upper Saddle River; Jon I. Klippel, Basking Ridge, all of N.J.

[73] Assignee: Howmedica, Inc., Rutherford, N.J.

[21] Appl. No.: 234,485

[22] Filed: Apr. 28, 1994

Related U.S. Application Data

[63] Continuation-in-part of Ser. No. 18,452, Feb. 14, 1994, abandoned, which is a continuation of Ser. No. 14,589, Oct. 26, 1993, abandoned.

[51] Int. Cl.$^6$ ............................................ A61F 2/36
[52] U.S. Cl. ............................................ 623/23; 623/18
[58] Field of Search ...................... 623/16, 18, 19, 623/20, 22, 23

[56] References Cited

U.S. PATENT DOCUMENTS

| | | | |
|---|---|---|---|
| 4,281,420 | 8/1981 | Raab | 623/23 |
| 4,283,799 | 8/1981 | Pratt, Jr. et al. | 623/23 |
| 4,336,618 | 6/1982 | Raab | 623/23 |
| 4,365,359 | 12/1982 | Raab | 623/23 |
| 4,491,987 | 1/1985 | Park | 623/23 |
| 4,536,894 | 8/1985 | Galante et al. | 623/23 |
| 4,566,138 | 1/1986 | Lewis et al. | 623/23 |
| 4,718,916 | 1/1988 | Morscher | 623/23 |
| 4,795,472 | 1/1989 | Crowninshield et al. | 623/23 |
| 4,827,919 | 5/1989 | Barbarito et al. | 623/23 |
| 4,881,536 | 11/1989 | Noble et al. | 623/23 |
| 5,092,900 | 3/1992 | Marchetti et al. | 623/23 |
| 5,108,452 | 4/1992 | Fallin | 623/23 |
| 5,258,035 | 11/1993 | Hofmann et al. | 623/23 |

FOREIGN PATENT DOCUMENTS

| | | | |
|---|---|---|---|
| 4125152 | 2/1993 | Sweden | 623/23 |

OTHER PUBLICATIONS

Clinical Orthopaedics and Related Research, *Collared and Precoated Femoral Stems*, Dec., 1992 (No. 285), pp. 81–83.
Biomat., Med. Dev., Art. Org. 6(4), 361–373 (1978), *Intramedullary Fixation of Implants Pre–Coated with Bone Cement: A Preliminary Study*, Park, et al.
Howmedica Surgical Techniques, *The Howmedica Precision Hip System*, Levy, et al.
Proceedings of the International Congress, Sep. 13–15, 1973, *The Knee Joint: Recent Advances in Basis Research and Clinical Aspects*, Ingwersen, et. al.

*Primary Examiner*—David Isabella
*Attorney, Agent, or Firm*—Pennie & Edmonds

[57] ABSTRACT

A prosthesis with an integral proximal spacer is described. The prosthesis has a base element with a textured surface to aid in adhesion to bone cement. The integral spacer has a generally tripod shape. A top circumferential portion at least partially surrounds the proximal end of the prosthesis, and three legs extend distally along the length of the prosthesis. Also disclosed is the process for making the prosthesis and spacer, which preferably involves injection molding of PMMA.

19 Claims, 6 Drawing Sheets

PROSTHESIS WITH INTEGRAL PROXIMAL SPACER

RELATED APPLICATIONS

The present application is a continuation-in-part of application Ser. No. 29/018,452, filed Feb. 14, 1994, now abandoned, which is a continuation of application Ser. No. 29/014,589, filed Oct. 26, 1993, now abandoned.

BACKGROUND OF THE INVENTION

The present invention relates to orthopaedic implants in general, and more particularly to a prosthesis used in conjunction with a cement spacer.

In hip replacement surgery, an enlarged canal is created through the reaming and broaching of the proximal femur and the subsequent removal of bone tissue. Bone cement is then inserted into the canal using standard methodology. Following the insertion of the bone cement, the implant must be inserted into the canal in a timely fashion with the proper alignment, before the bone cement cures. It is desirable to provide a prosthesis that can be easily implanted in the correct anatomical position and will therefore form a strong bond within a bone canal with the supplied bone cement.

It is known to provide implants with a coating of material to help bonding with bone cement in a bone canal. For example, in U.S. Pat. No. 4,283,799 to Pratt, Jr. etal., a pre-coated hip prosthesis is disclosed. All or most of the surface of the prosthesis is covered with a bone cement material that is bonded to the prosthesis. Similarly, U.S. Pat. No. 4,491,987 to Park discloses a prosthesis with a uniform polymer coating on substantially the entire surface of the prosthesis. In addition, U.S. Pat. Nos. 4,281,420 and 4,336,618 to Raab provide a prosthesis coated with a polymethylmethacrylate (PMMA) film fixedly adhered to the surface. The film is applied to the prosthetic surface after treating, and then the film is annealed. Similarly, U.S. Pat. No. 4,365,359 to Raab utilizes a silane coupling agent to adhere the PMMA film to a prosthetic element and further enhance the adherence of the prosthesis. A solid coating of bone compatible polymer around the proximal portion of a prosthesis is disclosed in U.S. Pat. No. 4,881,536 to Noble et al.

Another technique to increase the adherence of the prosthesis to the bone cement is the use of a textured surface on the prosthesis. An example of such a surface is shown in U.S. Pat. No. 4,795,472 to Crowninshield et al.

While the pre-coated and textured surfaces described above may assist a prosthesis in better adhering to the bone cement and bone, they do not provide certain other beneficial aspects of total hip replacement surgery including pressurization of the bone cement as the prosthesis is inserted and alignment of the prosthesis centrally within the bone canal.

Separate spacers for centralizing the prosthesis in the bone canal are disclosed in the art, for example in U.S. Pat. No. 4,827,919 to Barbarito et al. In use, such spacers are placed over the proximal opening of the bone canal either immediately before or after the bone cement is injected into the canal. The prosthesis is then inserted through the spacer into the canal. Such spacers have the disadvantage that, as the prosthesis is inserted, the bone cement is forced out of the canal and obscures the surgeon's view of the spacer, such that it is difficult to determine whether the prosthesis is properly seated. The spacer also has a slight tendency to lift up from the bone site due to the pressure of the expelled bone cement.

SUMMARY OF THE INVENTION

An object of the invention is to provide a prosthesis with an integral proximal spacer that allows for improved bonding, repeatable accuracy of placement of the prosthesis in a patient, and easier insertion of the prosthesis into the femoral canal.

An additional object of the invention is to provide a prosthesis with an integral proximal spacer that allows for improved pressurizing and aligning of the prosthesis within the bone cement in a bone canal. The prosthesis of the present invention is specifically directed for use in hip replacement surgery, with the prosthesis consisting of a hip femoral component that is inserted into the femur of a patient after removing the top portion and a central area of the femur. It is understood, however, that the concept of the present invention could be adapted for use in other orthopaedic surgery, such as knee surgery.

These and other objects are achieved according to the present invention by a combined prosthesis and integral, proximal spacer preferably made of a bone cement material molded onto the prosthesis. The spacer is shaped to pressurize the additional bone cement within the enlarged canal upon insertion, and to align the prosthesis centrally within the canal. In order to ensure a secure bond between the spacer and prosthesis shaft, a grit-blasted, textured surface is preferably provided on the prosthesis. For further bonding improvement, a series of dimples can be provided on the surface of the prosthesis. Also, a textured surface may be provided on the prosthesis adjacent the spacer for increased adherence to bone cement in the canal.

The integral bone cement spacer according to the present invention is preferably made by an injection molding process. The process includes the use of high pressure injection molding, using powdered and/or pelletized PMMA under heat and pressure to form the spacer around the prosthesis.

To prepare for the molding process, the prosthesis first undergoes a gas plasma cleaning process that prepares the surface of the prosthesis prior to the molding of the bone cement spacer. In this process, an energized oxygen and argon gas mixture removes any surface contaminants from the prosthesis and leaves the substrate surface "active", i.e. highly pure and devoid of contaminants. The process provides an extremely clean, contaminate-free surface for the prosthesis. The active surface ensures optimal bonding between the substrate and the molded PMMA. The prosthesis is then preheated via an induction heating process, prior to the high pressure molding process.

DETAILED DESCRIPTION

Figure 1:
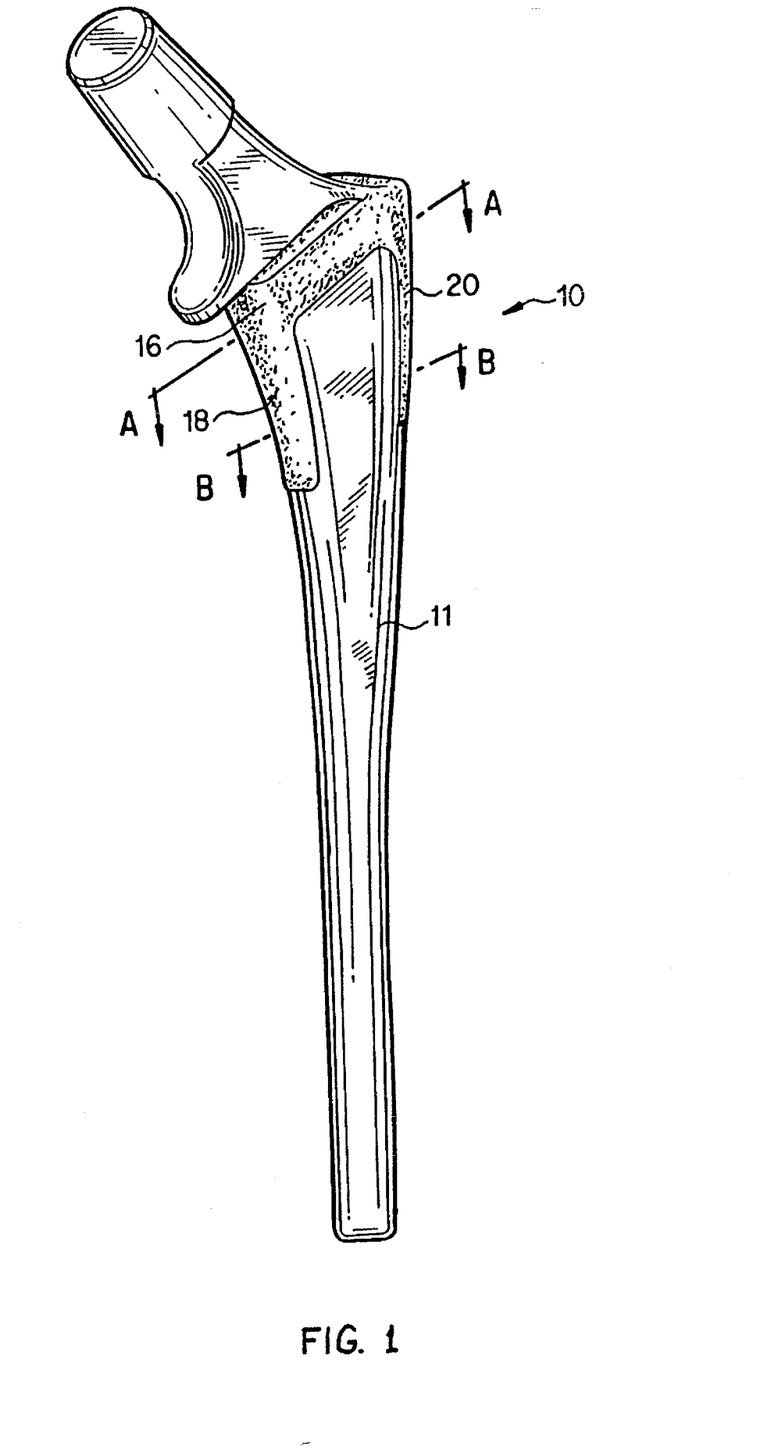
FIG. 1 is a perspective view of a prosthesis according to the invention illustrating the base element and integral spacer.

FIG. 1 illustrates a femoral prosthesis 10 comprising a prosthesis base element or shaft 11 with an integral proximal spacer 12 according to the present invention. The general shape of a femoral prosthesis is known and disclosed, for example, in U.S. Pat. No. 4,881,536 to Noble et al, which is incorporated herein by reference. The prosthesis base element is preferably constructed of a cobalt-chrome alloy, although other alloys are acceptable including stainless steel and titanium alloys.

Figure 2:
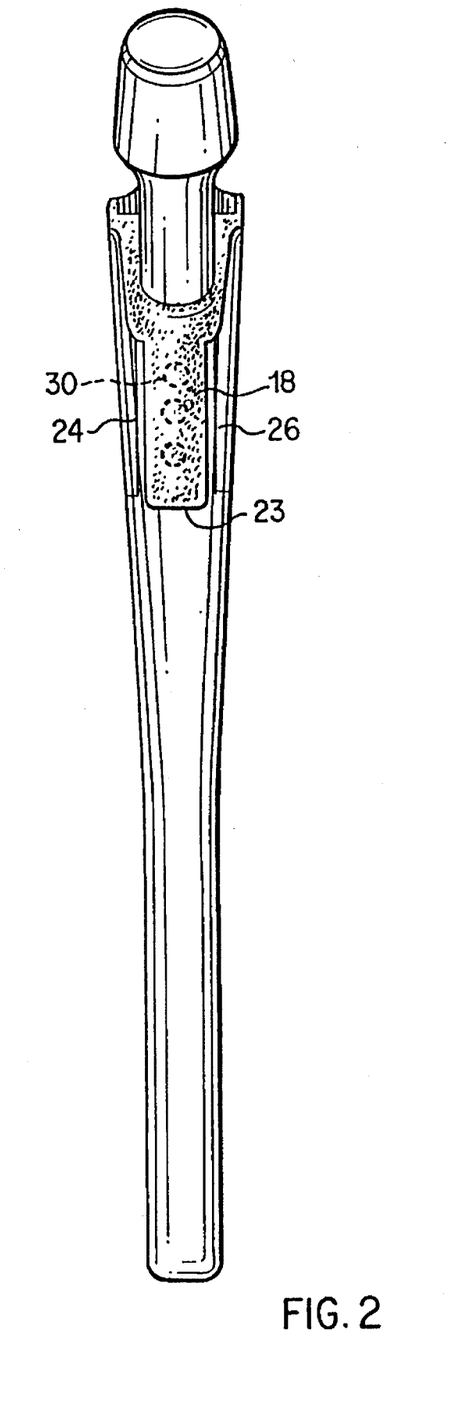
FIG. 2 is an medial view of the prosthesis of FIG. 1.
Figure 3:
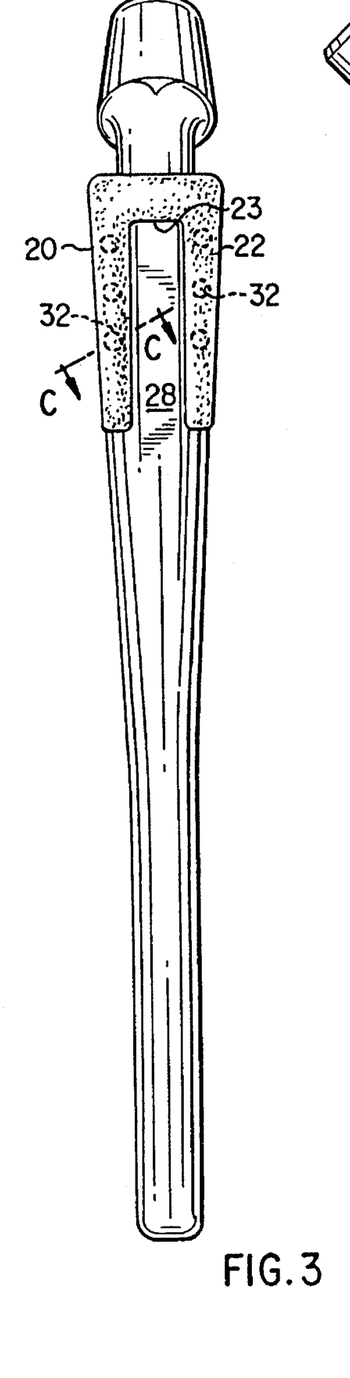
FIG. 3 is an lateral view of the prosthesis of FIG. 1.
Figure 4:
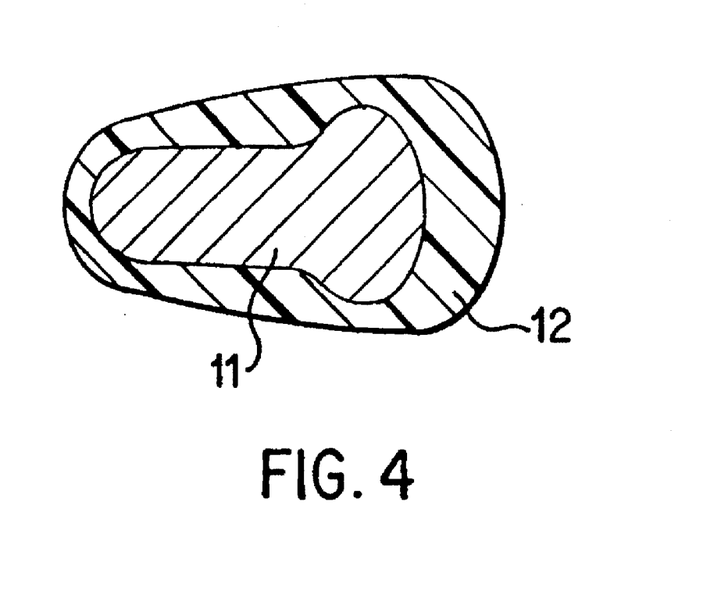
FIG. 4 is a cross-sectional view of the prosthesis through line A—A of FIG. 1.
Figure 5:
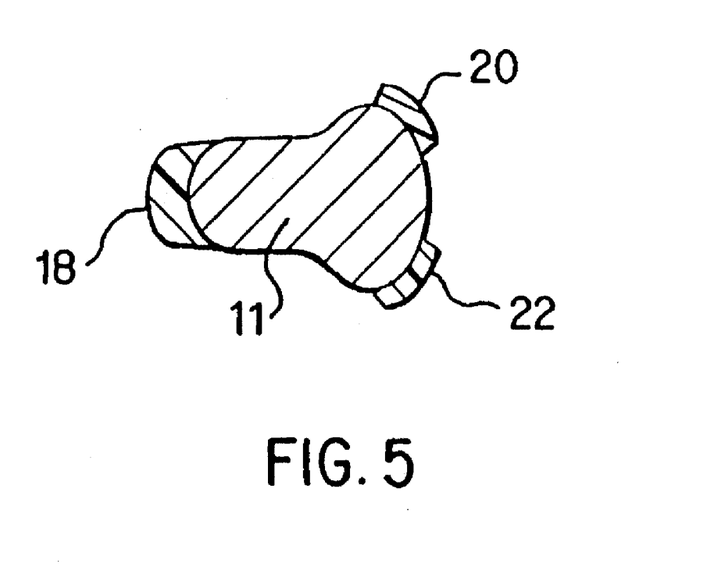
FIG. 5 is a cross-sectional view of the prosthesis through line B—B of FIG. 1.

Spacer 12 is illustrated in FIG. 1 as it appears affixed to the base element 11. The spacer has a circumferential portion 16 and, in this embodiment, three distally extending legs 18, 20, and 22. First leg 18 extends distally along the medial face of the prosthesis 10, as best shown in FIG. 2. The second leg 20 and third leg 22 extend distally along the lateral-anterior and lateral-posterior corners, as shown in FIG. 3. The legs preferably range in length from 0.600" to 1.125". Legs 18, 20, and 22 each have a gradually tapering shape ending in a feathered or tapered edge 23, which blends smoothly against the prosthesis substantially without discontinuity so as to create a surface that is inserted into a bone canal with little resistance and without catching on the edge of the canal. The configuration of the legs also prevents the formation of any voids or discontinuities within the additional cement supplied for implantation. The tapering is preferably approximately five degrees. Spacer 12 generally aids the surgeon in the correct alignment of the prosthesis within the bone canal, as the tapered legs 18, 20, and 22 allow for a gliding insertion, and the circumferential portion 16 assures final positioning. The cross-sectional views are shown in FIGS. 4 and 5.

Figure 11:
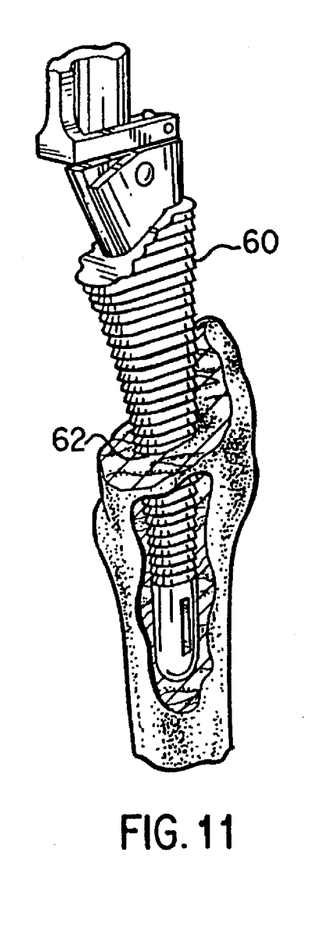
FIG. 11 is a perspective view of a bone canal broach sizing the femoral canal for insertion of the prosthesis of the invention.

To ensure correct alignment, the canal is preferably prepared, as shown in FIG. 11, with a bone canal broach 60 matched to the size of the prosthesis and integral spacer. The broach 60 and spacer are match-sized so as to create a substantially controlled distance between the circumferential portion 16 of the spacer and the bone canal opening 62. With the canal properly sized to match the spacer, circumferential portion 16 acts to pressurize the bone cement during the final insertion of the prosthesis and spacer into the bone canal.

Spacer 12 thus ensures neutral alignment of the prosthesis in the bone canal and the circumferential portion 16 helps to pressurize the bone cement within the canal. Excessive pressurization, however, is to be avoided to prevent blowout of the distal cement bone plug and difficulty in final implant seating. This problem is prevented in the present invention by the provision of the separate legs, preferably three legs 18, 20, and 22, which create spaces for cement "venting" as the prosthesis is introduced into the bone canal. This also allows the newly introduced cement to distribute evenly in the femoral canal. Final pressurization occurs only when circumferential portion 16 enters the canal and prevents further venting of cement. The spacer's tripod shape also allows for repeatable molding manufacture, and allows for reduced potential for voids or shrink to be present in the final molded article.

The unique shape of the bone cement spacer 12 provides other advantages for the implantation of the prosthesis. The "tripod" structure of relatively narrow circumferential portion 16 and three extending legs 18, 20, and 22 provides relief zones 24, 26, and 28 between the molded arms of the geometry, allowing for "gradual" alignment and pressurization upon insertion into the canal. This graduation assures a minimization of voids or discontinuities within the additional cement supplied to the bone canal for implantation. The circumferential portion is approximately 0.2–0.3 inches wide in the preferred embodiment, and the legs are approximately 0.3–0.5 inches wide.

Figure 9:
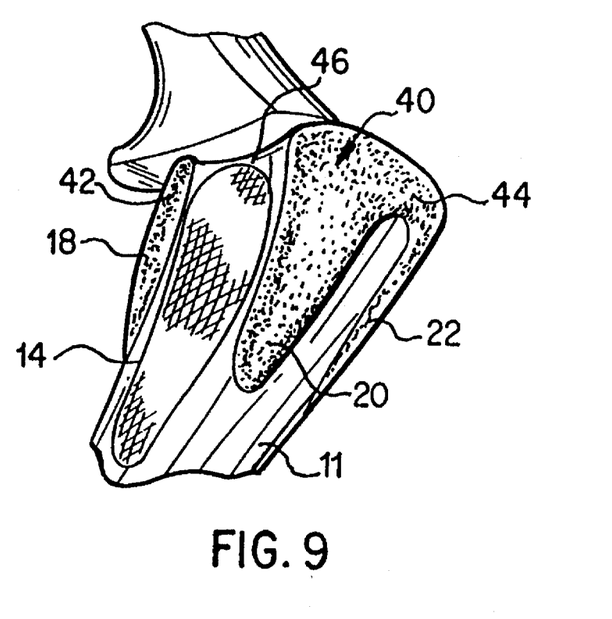
FIG. 9 is a perspective view of another alternative embodiment of the prosthesis according to the invention.
Figure 10:
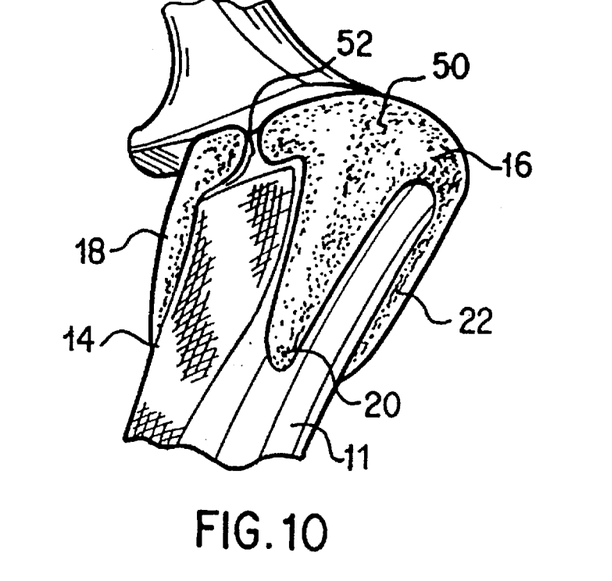
FIG. 10 is a perspective view of a further alternative embodiment of the present invention.

The prosthesis 10 is preferably provided with two areas of texture 14, one on the anterior side and one on the posterior side of base element 11 as shown in FIGS. 9 and 10. These areas are not covered by the spacer. The textured 14 areas are designed to provide very strong mechanical interlock at the locations where the prosthesis will be under significant amounts of torque rotation and stress between the prosthesis and bone cement. The texture can be in the form of a waffled macro-texture as shown by reference numeral 14, or, e.g., vertical grooves. The remaining surface of base element 11 has a slightly rough texture as is known in the art (such as formed by grit blasting).

Figure 8:
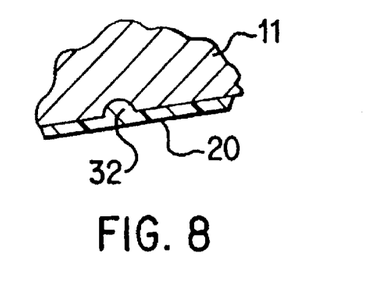
FIG. 8 is an enlarged cross-sectional view through line C—C in FIG. 3, showing a typical interlocking dimple.

The prosthesis is further preferably provided with a mechanical interlock between the spacer and base element. Base element 11 has a plurality of dimples, or concave hemispheres, located on the surface of the base element on the lateral and medial sides under the spacer. Referring to FIGS. 2 and 3, most preferably, there are three dimples 30 on the medial side, and six (two rows of three) dimples 32 on the lateral side. A cross-section of a typical dimple is illustrated in FIG. 8. A mechanical interlock is formed when the spacer is molded around the base element and flows into the dimples. The interlock is potentially strengthened by the shrink properties of the PMMA material used for the spacer as the PMMA cures onto the prosthesis. The key attributes of the dimples which maximize interlock are the location of the dimples, their depth, radius and angulation with respect to the stem surface.

Figure 6:
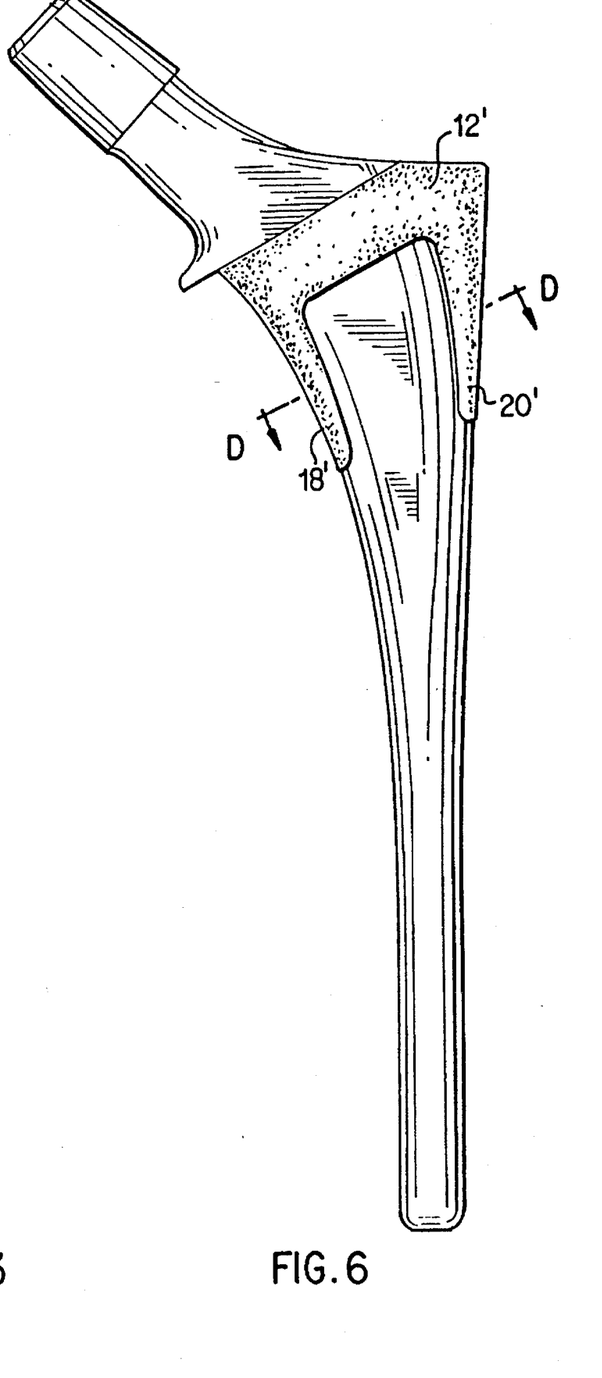
FIG. 6 is a side view of an alternative spacer attached to the prosthesis.
Figure 7:
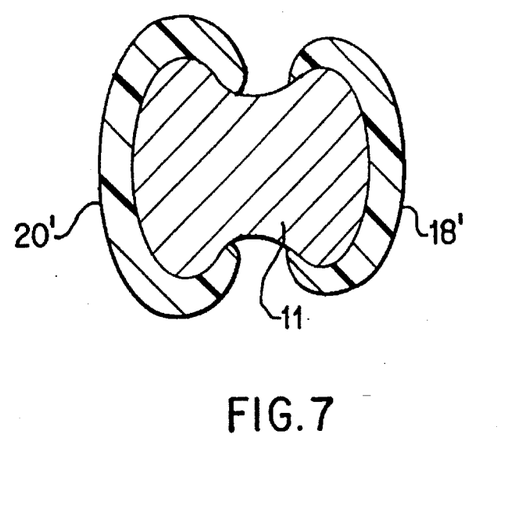
FIG. 7 is a cross-sectional view of the prosthesis through line D—D in FIG. 6.

FIGS. 6 and 7 illustrate an alternative embodiment in which only two extending legs are utilized. According to this alternative embodiment, spacer 12' is provided with only two distally extending legs: medial leg 18' and lateral leg 20'. FIG. 7 shows how the two distally extending legs 18', 20' of the alternative embodiment encompass the prosthesis. Spacer 12' is otherwise substantially the same as spacer 12.

Alternative structures also include designs that do not have a continuous ring around the upper portion of the spacer (FIG. 9) or are otherwise provided with vent holes or means to prevent overpressurization or control pressurization of the bone cement in the canal when the prosthesis is inserted (FIG. 10). Spacer 40, shown in FIG. 9, has a medial portion 42 which is completely separate from lateral portion 44. Medial leg 18, as previously described, is within medial portion 42 and, similarly, lateral legs 20, 22 are in lateral portion 44. Gap 46 between portions 42 and 44 prevents pressurization, while legs 18, 20 and 22 ensure proper centralization. Spacer 50, shown in FIG. 10, has vents 52 formed in circumferential portion 16 along the posterior and anterior sides to prevent or control pressurization. The size of vents 52 can be changed to vary the amount of pressurization of the bone cement as the prosthesis is inserted into the bone canal by controlling the amount of bone cement that is expelled. Again, legs 18, 20 and 22 ensure proper centralization. These embodiments for reducing or eliminating pressurization also may be employed with a two-legged spacer as shown in FIG. 6.

In each of the embodiments, the spacer is preferably injection molded directly onto the base element, to provide an integral, single piece prosthesis for implantation and to ensure a strong bond between the base element and the spacer. The manufacturing process involves preparing the base element for the molding, and then molding the spacer thereon. To prepare the base element for molding, it is subjected to a gas plasma cleaning process. Preferably, a Gas Plasma Unit Model C-24 from Advanced Plasma Systems, Inc. is utilized. The gas plasma unit applies an ionized mixture of oxygen and argon gases (40% $O_2$ and 60% Ar) to the prosthesis, which provides a clean, active, oxidized surface that is extremely wettable and allows the molded material to adhere to the prosthesis easily.

In use of the-gas plasma unit, the prosthesis is placed on a fixture to hold the element, and placed in a chamber. The chamber is then closed, and evacuated to 225 millitorr. The gas mixture of 40% $O_2$ and 60% Ar is then added. The plasma field is energized by a 950 watt R.F. Fresh gases are circulated through the chamber at a rate of 0.5 S.L.M. After twenty minutes of R.F., the chamber is purged with nitrogen gas.

The prosthesis and the supporting fixture is then placed in an induction heater and preheated to about 500° F. +/−50° F., and then placed directly into the mold, such that the prosthesis does not drop significantly in temperature. Preheating the prosthesis before the molding step enhances the cement to substrate transition at the critical end points of the molded geometry. The raised temperature of the prosthesis provides a neutral environment for the PMMA attachment and for uniform cooling of the prosthesis and spacer.

The spacer is preferably molded from commercial grade PMMA (which may be in pelletized/granular form or a finer powdered form) blended with about 7% by weight $BaSO_4$ powder that has been extruded into pellets. The mold itself is modular to fit all stem sizes. The outer portion of the mold is made of stainless steel, and the inner portion is a flexible elastomeric liner that prevents the prosthesis from being scratched or deformed and allows spacers of different dimensions to be molded under high pressure. The elastomeric liner also allows for the formation of the geometry of the 4 legs of the spacer. These geometries would be difficult to create using conventional stainless steel molds. In the molding process, the raw material is loaded into a sealed hopper, and the mold is preheated to 120° F. +/− 10° F. The preheated prosthesis is placed into the preheated mold cavity, and the mold is closed and the molding cycle begins. The initial pressure is built up to 1500 psi, and the mold is filled to a certain volume with the raw material. The pressure is reduced to 250 psi until the complete fill of the mold is achieved. The pressure is held until the mold cavity pressure starts to decrease. The pressure drops to zero, and the clamp pressure is maintained until the part solidifies, and the prosthesis can be ejected. The molded spacer is then trimmed as necessary with a hot knife.

For final finishing, the prosthesis is inspected visually using X-rays, and sterilized with gamma irradiation.

As an alternative, molding can be accomplished at lower temperature and pressure by first mixing the bone cement powder with a curing agent and injecting the liquid bone cement into the mold to harden.

We claim:

1. A prosthesis comprising:
   an elongated base element with a proximal end and a distal end for insertion into a bone canal; and
   a spacer member secured to the base element with a circumferential portion at least partially surrounding the proximal end of said base element, said circumferential portion having a distal edge, said spacer member further having at least two separate legs, each of said legs extending distally from the distal edge of said circumferential portion along the base element, said legs tapering to a reduced thickness and width in the distal direction wherein the spacer member allows for improved pressurization and aligning of the prosthesis within the bone canal.

2. The prosthesis of claim 1 wherein said legs are tapered to provide distal edges that blend with the base element that facilitate insertion.

3. The prosthesis of claim 1 wherein said circumferential portion completely surrounds the proximal end of the base element.

4. The prosthesis of claim 3 wherein said circumferential portion has a tapered distal edge to facilitate insertion into the bone canal.

5. The prosthesis of claim 1 wherein said circumferential portion defines at least one vent space to allow escape of bone cement as the prosthesis is inserted into the bone canal to prevent excessive pressurization of bone cement in the canal.

6. The prosthesis of claim 1 wherein the base element defines at least one depression therein disposed under the spacer member such that a part of said spacer member extends into the depression to create a mechanical interlock therebetween.

7. The prosthesis of claim 6 wherein said base element defines a plurality of said depressions with at least one said depression disposed under each leg of said spacer member.

8. The prosthesis according to claim 1, wherein:
   said base element is configured and dimensioned for insertion into a femoral bone canal as a shaft of a femoral prosthesis; and
   at least two of said legs comprise a first leg extending distally along the medial face of the prosthesis shaft and at least a second leg extending distally along the lateral face of the prosthesis shaft.

9. The prosthesis of claim 8 wherein at least said second leg extends distally along the lateral-anterior surface of the shaft;
   said spacer member further comprises at least a third leg extending distally along the lateral-posterior surface of the shaft wherein said second and third legs terminate at spaced apart distal ends.

10. The prosthesis of claim 9 wherein the base element defines a plurality of depressions therein with at least one said depression disposed under each leg of the spacer member such that a part of each leg extends into said at least one depression to create a mechanical interlock therebetween.

11. The prosthesis of claim 10, wherein there are at least three said depressions arranged in a row under each said leg.

12. The prosthesis of claim 1 wherein said spacer member comprises first and second separate parts, each said part defining a part of said circumferential portion such that a gap is defined between the respective parts of the circumferential portion, each said part comprising at least one said distally extending leg.

13. A prosthesis implantation kit, comprising the prosthesis of claim 3 in combination with a bone canal broach, wherein said circumferential portion of the prosthesis spacer member defines an outer profile and said broach defines an outer broach profile configured and dimensioned to broach the bone canal to substantially match said circumferential portion outer profile for controlled clearance between the bone canal and spacer member such that bone cement deposited in the canal is pressurized when the prosthesis is inserted therein and seated against the broached canal.

14. A prosthesis comprising:
 a base element with a proximal and distal end for insertion into a bone canal;
 a spacer member bonded to the base element comprising a circumferential portion which surrounds the proximal end of said base element, said circumferential portion having a distal edge; and
 a medial leg and two lateral legs each joined to said circumferential portion of said spacer member at said distal edge and extending distally wherein the spacer member allows for improved pressurization and aligning of the prosthesis within the bone canal.

15. The prosthesis of claim 14 wherein the legs are tapered to provide distal edges that blend with the base element to facilitate insertion of the prosthesis.

16. The prosthesis of claim 14 wherein the spacer is formed by molding PMMA directly onto the prosthesis.

17. The prosthesis claim 14 further comprising a plurality of concave hemispheres formed in the medial and lateral sides of said base element, said hemispheres receiving protrusions of said spacer to create an improved bond between the spacer and the base element.

18. The prosthesis of claim 14 further comprising an area of textured surface over a portion of the base element between said legs.

19. The prosthesis of claim 14 wherein said base element is constructed of a cobalt-chrome alloy, titanium alloy, or stainless steel alloy.

* * * * *

REEXAMINATION CERTIFICATE (nd)

United States Patent [19]
Michielli et al.

[11] B1 5,507,832
[45] Certificate Issued Jul. 27, 1999

[54] PROSTHESIS WITH INTEGRAL PROXIMAL SPACER

[75] Inventors: Michael Michielli, Hoboken; Glen Kashuba, River Edge; J. Mel Goldenberg, Upper Saddle River; Jon I. Klippel, Basking Ridge, all of N.J.

[73] Assignee: Howmedica, Inc., Rutherford, N.J.

Reexamination Request:
No. 90/004,587, Mar. 17, 1997

Reexamination Certificate for:
Patent No.: 5,507,832
Issued: Apr. 16, 1996
Appl. No.: 08/234,485
Filed: Apr. 28, 1994

Related U.S. Application Data

[63] Continuation-in-part of application No. 29/018,452, Feb. 14, 1994, abandoned, which is a continuation of application No. 29/014,589, Oct. 26, 1993, abandoned.

[51] Int. Cl.⁶ .................................................... A61F 2/36
[52] U.S. Cl. .................................................... 623/23; 623/18
[58] Field of Search .............................. 623/16, 18, 19, 623/20, 22, 23

[56] References Cited

U.S. PATENT DOCUMENTS

| | | |
|---|---|---|
| D. 243,286 | 2/1977 | Deyerle . |
| D. 339,634 | 9/1993 | Hori et al. . |
| D. 342,570 | 12/1993 | Serbousek et al. . |
| 3,320,951 | 5/1967 | Wittebol . |
| 4,038,703 | 8/1977 | Bokros . |
| 4,612,160 | 9/1986 | Donlevy . |
| 4,728,335 | 3/1988 | Jurgutis . |
| 4,753,657 | 6/1988 | Lee et al. . |
| 4,790,852 | 12/1988 | Noiles . |
| 4,804,431 | 2/1989 | Ribner . |
| 4,842,606 | 6/1989 | Kranz et al. . |
| 5,007,931 | 4/1991 | Smith . |
| 5,018,285 | 5/1991 | Zolman et al. . |
| 5,047,054 | 9/1991 | Vijayan . |
| 5,089,004 | 2/1992 | Averill . |
| 5,094,076 | 3/1992 | Henricks . |
| 5,116,380 | 5/1992 | Hewka et al. . |
| 5,344,494 | 9/1994 | Davidson et al. . |
| 5,370,696 | 12/1994 | Jamison et al. . |
| 5,415,726 | 5/1995 | Staller et al. . |

FOREIGN PATENT DOCUMENTS

| | | |
|---|---|---|
| 149527 | 7/1985 | European Pat. Off. . |
| 321389 | 6/1989 | European Pat. Off. . |
| 385585 | 5/1990 | European Pat. Off. . |
| 466638 | 1/1992 | European Pat. Off. . |
| 501116 | 2/1992 | European Pat. Off. . |
| 2668058 | 4/1992 | France . |
| 4125152 | 2/1993 | Germany . |
| 2142830 | 1/1985 | United Kingdom . |
| 93 01770 | 2/1993 | WIPO . |

*Primary Examiner*—David J. Isabella

[57] ABSTRACT

A prosthesis with an integral proximal spacer is described. The prosthesis has a base element with a textured surface to aid in adhesion to bone cement. The integral spacer has a generally tripod shape. A top circumferential portion at least partially surrounds the proximal end of the prosthesis, and three legs extend distally along the length of the prosthesis. Also disclosed is the process for making the prosthesis and spacer, which preferably involves injection molding of PMMA.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–19 is confirmed.

\* \* \* \* \*